United States Patent
Stepp et al.

(10) Patent No.: US 8,520,919 B2
(45) Date of Patent: Aug. 27, 2013

(54) APPARATUS AND METHOD FOR CONTROLLING A MULTI-COLOR OUTPUT OF AN IMAGE OF A MEDICAL OBJECT

(75) Inventors: Herbert Stepp, Planegg (DE); Hilmar Schachenmayr, Clarkson (AU)

(73) Assignee: Karl Storz GmbH & Co. KG (DE)

( * ) Notice: Subject to any disclaimer, the term of this patent is extended or adjusted under 35 U.S.C. 154(b) by 695 days.

(21) Appl. No.: 12/817,646

(22) Filed: Jun. 17, 2010

(65) Prior Publication Data

US 2010/0322492 A1  Dec. 23, 2010

(30) Foreign Application Priority Data

Jun. 17, 2009  (DE) .......................... 10 2009 025 662

(51) Int. Cl.
| | |
|---|---|
| G06K 9/00 | (2006.01) |
| A61B 1/04 | (2006.01) |
| A61B 1/06 | (2006.01) |
| A61B 6/00 | (2006.01) |
| H04N 15/00 | (2006.01) |
| H04N 3/14 | (2006.01) |
| H04N 9/04 | (2006.01) |
| G01J 5/02 | (2006.01) |

(52) U.S. Cl.
USPC .......... 382/128; 600/112; 600/160; 600/178; 600/181; 600/476; 348/42; 348/45; 348/275; 250/350

(58) Field of Classification Search
USPC ........... 382/128; 600/160, 178, 476; 348/45
See application file for complete search history.

(56) References Cited

U.S. PATENT DOCUMENTS

| | | | |
|---|---|---|---|
| 5,266,805 A * | 11/1993 | Edgar | 250/330 |
| 6,970,597 B1 * | 11/2005 | Olding et al. | 382/167 |
| 2001/0033326 A1 * | 10/2001 | Goldstein et al. | 348/42 |
| 2005/0065406 A1 | 3/2005 | Cline et al. | |
| 2005/0143627 A1 * | 6/2005 | Cline et al. | 600/181 |
| 2007/0159640 A1 | 7/2007 | Berestov | |
| 2008/0177140 A1 * | 7/2008 | Cline et al. | 600/112 |
| 2008/0239070 A1 | 10/2008 | Westwick et al. | |
| 2008/0267526 A1 * | 10/2008 | Mitsunaga et al. | 382/274 |
| 2009/0041368 A1 | 2/2009 | Leberl et al. | |
| 2009/0066821 A1 * | 3/2009 | Achong et al. | 348/273 |
| 2010/0149403 A1 * | 6/2010 | Wang et al. | 348/335 |
| 2010/0283874 A1 * | 11/2010 | Kinrot | 348/242 |

FOREIGN PATENT DOCUMENTS

| | | |
|---|---|---|
| EP | 1535568 A1 | 6/2005 |
| WO | 2009117483 A1 | 9/2009 |

OTHER PUBLICATIONS

Foveon, "X3 Direct Image Sensors" Septemter 13, 2008.*
Shleif, Rober, "Sensing Violet" from website Apr. 20, 2008.*
European Search Report; Application No. EP 10 00 6013; Sep. 16, 2010; 6 pages.

* cited by examiner

*Primary Examiner* — Neal Sereboff
(74) *Attorney, Agent, or Firm* — St. Onge Steward Johnston & Reens LLC

(57) ABSTRACT

In a method for controlling a multi-color output of an image of a medical object for assisting medical personnel, the medical object is illuminated with light with an illumination spectrum. By means of an image sensor, image data are acquired for a group of one or more color channels. Image information concerning an additional color channel, which is not among the group of one or more color channels, is generated depending on the acquired image data. An image output device for multi-color output of the image is controlled depending on the acquired image data and the acquired image information.

14 Claims, 3 Drawing Sheets

APPARATUS AND METHOD FOR CONTROLLING A MULTI-COLOR OUTPUT OF AN IMAGE OF A MEDICAL OBJECT

CROSS-REFERENCE TO RELATED APPLICATIONS

The present application claims priority of German patent application No. 10 2009 025 662.8 filed on Jun. 17, 2009, the content of which is incorporated herein by reference.

FIELD OF THE INVENTION

The present invention relates to a method and an apparatus for controlling a multi-color output of an image of a medical object.

BACKGROUND OF THE INVENTION

In some imaging diagnostic methods, an image of a medical object illuminated with white light and an image of the medical object are acquired in fluorescent light either simultaneously or sequentially. Such methods include photodynamic diagnosis (PDD) and fluorescent endoscopy with indocyanine green (ICG). Two video cameras are customarily used for this process. A first video camera acquires the image resulting from the illumination of the medical object with white light in the visible spectral range, and a second video camera acquires the fluorescent light. Both video cameras can be coupled, for instance by a dichroic mirror, with a single endoscope or a single lens in order to acquire both images from the same perspective.

The use of two video cameras doubles the equipment outlay. In particular, two frame grabbers or video grabbers or image-grabbing switches are necessary for digitizing the video signals of both video cameras. With the computing capacities of computers employed in medical technology today, two separate systems are required for real time processing of the two resulting video streams. The data volume that is to be stored is also doubled and accordingly makes demands on data rates and storage capacities.

If, however, a single video camera system is used for acquiring the image in white light as well as the image in fluorescent light, then the two images can be acquired only in alternation. On switching between the two modes, it is at least necessary to replace observation filters. For instance, in observing the fluorescent light, as a rule one filter is necessary, which blocks the remitted portions of the light used to excite the fluorescence (hereafter referred to as excitation light). Even in cases where a non-simultaneous alternating acquisition of an image and of an image in fluorescent light is acceptable, the requirement to replace the observation filter poses an insuperable technological obstacle. For instance, it is not yet possible to integrate a device for replacing the observation filter on the distal end of a video endoscope.

SUMMARY OF THE INVENTION

One object of the present invention consists in creating an improved method and an improved apparatus as well as a corresponding computer program for controlling a multi-color output of an image of a medical object.

This object is achieved through the objects of the main patent claims.

Refinements are indicated in the subsidiary patent claims.

Various embodiments of the present invention are based on the recognition that even in medical applications, only a fraction of the color spectrum is made use of, and on the idea of using one of the typical three or four color channels of a video camera for the acquisition of fluorescent light and reconstructing image information of this color channel, which is lost for the white light depiction, from the image data of the remaining color channels. It is often possible to achieve a very natural-looking color depiction on the basis of customary and statistically evaluated correlations between color values in relevant image areas or for relevant objects, with the reconstructed color channel or the imitated color values for the color channel used for acquiring the fluorescent light.

In diagnostic or therapeutic activity, and especially in surgical activity, medical personnel must simultaneously obtain and evaluate a great deal of information. Medical personnel can be supported and relieved by a natural-looking color depiction, which also can relieve the strain of concentrating on the information that is actually relevant.

Thus, instead of two image sensors or video camera systems—one each for the acquisition of an image in white light and for the acquisition of an image in fluorescent light—only one (multi-colored) image sensor or one video camera system (possibly with one dichroic-acting prism and several image sensors mounted on the prism) needs to be used. To differentiate fluorescent light and remitted white light, the filter layers of the multi-color image sense or of the dichroic reflection properties of the prism of a multi-chip video camera are used, in particular in combination with an adjusted filter design. This adjusted filter design ensures, in particular, that fluorescent light is acquired only by one color channel, while the remaining color channels acquire no fluorescent light but rather, at least approximately, acquire the light that they would acquire normally with illumination by white light. This takes into account the fact that the color channel used for acquiring the fluorescent light is lost for acquiring the image in white light and the related color values, as mentioned, are reconstructed.

Depending on the application and the corresponding choice of model, the embodiments of the present invention offer a series of advantages. In particular, it becomes possible as a rule to dispense with two separate video camera systems for depicting a white light image and a fluorescent light image. The demands in terms of equipment are hereby reduced by half, and in particular only one image, or the video stream of a single video camera, must be acquired, digitized, processed, and stored.

An additional advantage often consists in the fact that a change of observation filter is not required. Therefore the present invention can also be implemented, for instance, in the form of a video endoscope (that is, with image sensor on the distal end of the endoscope). If no change of observation filter is required, simultaneous acquisition of an image in fluorescent light and of a (partially reconstructed) image in white light often becomes possible as well. The present invention can be used both with a video camera having a single multi-color image sensor and with a multi-chip video camera with dichroic separation of color channels.

With a method for controlling a multi-color output of an image of a medical object to assist medical personnel, the medical object is illuminated with light with an illumination spectrum. For a group of one or more color channels, image data, in particular color values, are acquired by means of an image sensor. Depending on the acquired image data, it is especially possible to calculate image information, in particular color values, concerning an additional color channel that is not among the group of one or more color channels. Depending on the acquired image data and the generated image information, an image output device for multi-color output of the image is controlled.

The illumination spectrum is, for instance, a white spectrum or a spectrum that is perceived as white by the human eye. The illumination of the medical object and the acquisition of image data can proceed by means of one or two separate endoscopic probes. For an image sensor with three or four color channels, the group includes two or three color channels.

Image information concerning the additional color channel for an image point or a pixel or image cell is generated, for instance, depending on the image data acquired for the group of one or more color channels for this image point and/or depending on image data acquired for the group of one or more color channels for surrounding image points. Image information for an image point, in addition, can be generated depending on image data acquired at various times. In particular, if successive image data are acquired for several images of the medical object in the form of a video recording, the medical object or a part of the medical object can at least be either identified or tracked in the several images in order to associate image points with the medical object or with the part of the medical object in each of several images. Image information for an image point can then be generated according to whether the image point is assigned to the medical object or to the part of the medical object. In this way various functions or algorithms or parameters can be used to generate image information for various objects or parts of objects within the image.

A lookup table or a mathematical function, in particular, can be used to generate image information. To produce the lookup table or mathematical function, reference image data are acquired for the group of one or more color channels and for the additional color channel with illumination of one reference object with white light or light with another predetermined spectrum. A correlation is ascertained between reference image data for the additional color channel and reference image data for the group of one or more color channels. On the basis of the correlation expressed, for instance as a lookup table or in the form of a mathematical function, image information can be generated concerning the additional color channel depending on the image data acquired for the group of one or more color channels.

The reference object can be a typical object with respect to its reciprocal interaction with light with the predetermined spectrum for objects to be configured. The correlation can also be ascertained on the basis of the reference image data of several reference objects. Alternatively, the reference object is the object, so that the reference image data for an illumination situation foreseen for the purpose are acquired with the predetermined spectrum.

In one of the described methods, moreover, simultaneously or in alternation with the illumination with light with the illumination range, the object can be illuminated with light with an excitation spectrum that differs from the illumination spectrum. By means of the image sensor or another image sensor, additional image data can be acquired for the additional color channel, and in particular fluorescent light is acquired from the objects. The image output device can be controlled depending on the acquired additional image data or on the acquired image data, the generated image information, and the acquired additional image data. The fluorescent light is generated, for instance, in the fluorescence of indocyanine green (ICG).

The described methods in particular can be executed with just one video camera, wherein the video camera comprises an image sensor for several image channels or several image sensors for one color channel each.

The present invention can be implemented as a method or as a computer program with program code for executing or controlling such a method, if the computer program runs on a computer or a processor. In addition, the invention can be implemented as a computer program product with a program code that is stored on a mechanically readable carrier (such as an ROM, PROM, EPROM, EEPROM, or flash memory, a CD-ROM, DVD, HD-DVD, Blue Ray DVD, diskette or hard disc), or stored in the form of firmware, for executing one of the aforementioned methods if the computer program product runs on a computer, calculator or processor. In addition, the present invention can be implemented as a digital storage medium (such as ROM, PROM, EPROM, EEPROM, or flash memory, CD-ROM, DVD, HD-DVD, Blue Ray-DVD, diskette or hard disc) with electronically readable control signals, which can interact with a programmable computer or processor system in such a way that one of the described methods is executed.

In addition, the present invention can be implemented as an apparatus, where the apparatus is configured to execute one of the methods here described, or where the apparatus includes a computer program, a computer program product, or a digital storage medium as described in the preceding paragraph.

An apparatus for controlling a multi-color output of an image of a medical object includes one or more image sensors for acquiring image data, especially color values, for a group of one or more color channels, a reconstruction device, and a control. The reconstruction device is coupled with an output of the one or more image sensors and configured so as to generate image information, in particular color values, concerning an additional color channel that is not included among the group of one or more color channels, depending on the acquired image data. The control is coupled with the output of the one or more image sensors and with an output of the reconstruction device and configured so as to control an image output device for multi-color output of the image depending on the acquired image data and the generated image information.

The apparatus can, in addition, include an illuminating device for alternating or simultaneous illumination of the medical object with light with an illumination spectrum and with light with an excitation spectrum that differs from the illumination spectrum. The one or more image sensors here are, in addition, configured to acquire image data for the additional color channel. The control, in addition, is therefore configured to control the image output device depending on the acquired additional image data or depending on the acquired image data, the generated image information, and the acquired additional image data.

BRIEF DESCRIPTION OF THE DRAWINGS

Hereafter, embodiments are described in greater detail with reference to the appended illustrations.

DETAILED DESCRIPTION OF THE INVENTION

Figure 1:
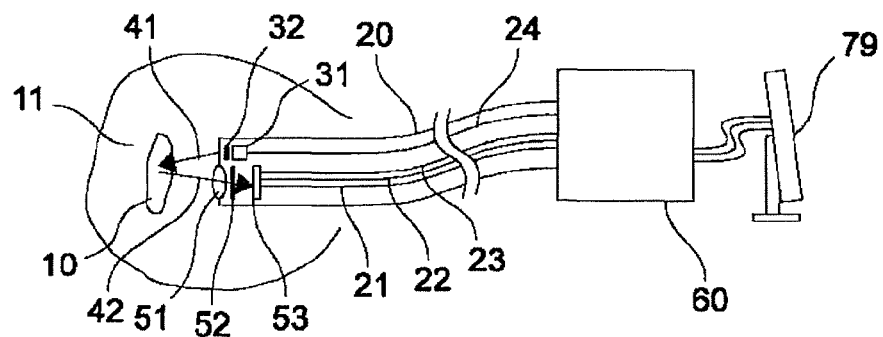
FIG. 1 is a schematic depiction of a medical object and an endoscopic apparatus.

FIG. 1 is a schematic depiction of a medical object 10 in a hollow space 11, for example a patient's oral cavity, and of an endoscopic apparatus. The endoscopic apparatus includes an endoscope 20 with signal lines 21, 22, 23 and an illumination line 24. A light source 31 with an illumination filter 32 and a lens 51, an observation filter 52, and an image sensor 53 are positioned on a distal end of the endoscope 20. The light source 31 is connected with the illumination line 24 in order to receive electric current over this line. The image sensor 53 is coupled with the signal lines 21, 22, 23, whose number can differ from three.

Figure 2:
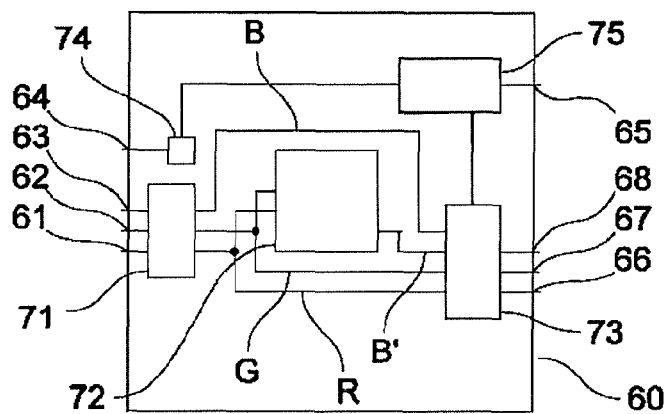
FIG. 2 is a schematic depiction of an apparatus for controlling a multi-color output.

One proximal end of the endoscope 20 is coupled with an apparatus 60 for control, which is described more closely hereafter with reference to FIG. 2. The apparatus 60 is coupled with an image output device 79, for instance a screen or monitor. The light source 31 and the illumination filter 32 are configured so as to cast light 41 with an illumination spectrum onto the medical object 10. The light 41 can have portions in the ultraviolet, visible, or infrared spectral range. The lens 51 is configured in order to focus light 42 remitted or emitted by the object 10 onto the image sensor 53 and thus to configure the medical object 10 onto the image sensor 53. Properties of the illumination filter 32 and of the observation filter 52 are described in more detail hereafter with reference to FIGS. 3 and 4.

The three signal lines 21, 22, 23 transmit signals, for example, that each depict the color values to one of three color channels of the image sensor 53. For example the first signal line 21 transmits the R signal, the second signal line 22 the G signal, and the third signal line 23 the B signal of the image sensor 53, if the latter is an RGB sensor. This type of signaling makes possible a particularly vivid depiction, precisely with respect to FIG. 2. In fact, however, the present invention depends on the way in which image data are transmitted from the image sensor 53 to the apparatus 60. This can occur in compressed or non-compressed form, electrically or optically, and separated by color channels or with signals that contain several or all color channels. In addition, the present invention is independent of the color space in use. In particular, instead of the RGB, HSV, HSI, HSL, CMYK, LMS, XYZ, Lab color space, any other color spaces can be employed. The color spaces used by the image sensor 53 in the reconstruction or preparation described hereafter and by the image output device 79 can be identical to or different from one another. However, a reconstruction or preparation in the original color space of the image sensor 53 is advantageous as a rule.

Some aspects of the present invention, in addition, are independent of whether the image sensor 53, as shown in FIG. 1, is situated on the distal end of the endoscope 20 or on its proximal end or in the apparatus 60. In addition, the light source 31 can be positioned on the distal end of the endoscope 20 or on its proximal end or in the apparatus 60. In this case the light from the light source 31 is transmitted, for instance by light wave lines, to the distal end of the endoscope 20, such that the illumination filter 32 can be positioned close to the light source 31, on the distal end of the endoscope 20, or in between. Depending on where the light source 31 is placed, it can include, for instance, one or more light diodes, lasers, xenen gas discharge lights, halogen metal halide lamps, mercury halide lights, halogen light bulbs. Instead of the illumination filter 32, the light source 31 itself can comprise a corresponding spectral characteristic. Instead of one light source 31, it is possible to provide several light sources, which generate various spectra in alternation or simultaneously. The proximal end of the endoscope 20, as shown in FIG. 1, can be connected with the apparatus 60 directly or via electrical and/or optical lines.

FIG. 2 shows a schematic depiction of the apparatus 60 for controlling a multi-color output of the medical object 10. The apparatus 60 comprises a first signal input 61 coupled with the first signal line 21, a second signal input 62 coupled with the second signal line 22, a third signal input 63 coupled with the third signal line 23, and an illumination input 64 coupled with the illumination line 24. In addition, the apparatus 60 comprises a control input 65 and three signal outputs 66, 67, 68 for connecting with the image output device 79. The control input 65 is configured for connection, for example, with a keyboard, a mouse, or other service devices of a user interface. Similarly to the three signal lines 21, 22, 23 of the endoscope 20 and the three signal lines 61, 62, 63 of the apparatus 60, the signal outputs 66, 67, 68 of the apparatus 60 can each be associated with one of three color channels R, G, B. However, the image output device 79 can also be controlled in other ways.

The apparatus 60 further includes a signal preparation device 71, a reconstruction device 72, an output control 73, an illumination control 74, and a mode control 75. The signal preparation device 71 includes, for instance, input amplifiers, decoding devices, coding devices, analog-digital converters, and/or a device for converting image data or color values from one color space into another color space. The output control 73 includes, for instance, devices for converting color values from one color space into another color space, devices for mixing or replacing colors, digital-analog converters, and/or output amplifiers. The illumination control 74 is configured to control the light source 31 or, in some cases, several light sources. The mode control 75 is coupled with the control input 65, the output control 73, and the illumination control 74.

Outputs from the signal preparation device 71 are coupled to the inputs of the reconstruction device 72 and the output control 73. One or more outputs from the reconstruction device 72 are coupled with one or more inputs of the output control 73.

The reconstruction of a color channel by the reconstruction device 72, as described below, is independent both of the selected color spaces and of the type of signaling of color values outside and inside the apparatus 60. Hereafter, only for purposes of clear visual depiction, the signal lines 21, 22, 23 of the endoscope 20, the signal inputs 61, 62, 63 and the signal outputs 66, 67, 68 of the apparatus 60, and the lines shown inside the apparatus 60 in FIG. 2 between the signal preparation device 71, the reconstruction device 72, and the output control 73 are each associated with one R, G, B color channel. This arrangement is indicated as an example in FIG. 2, and the color channel B' is explained below.

In the following, it is assumed by way of example that signal R (red signal) is transmitted by the first signal line 21 of the endoscope 20 and the first signal input 61 of the apparatus 60, signal G (green signal) is transmitted by the second signal line 22 of the endoscope 20 and the second signal input 62 of the apparatus 60, and signal B (blue signal) is transmitted by the third signal line 23 of the endoscope 20 and the third signal input 63 of the apparatus 60. In addition, the color channel B of the image sensor 53 is used to acquire fluorescent light, so that it is no longer available for acquiring an image by illumination with white light.

After preparation by the signal preparation device 71, the R and G signals are conducted to the output control 73 and in parallel to the reconstruction device 72. On the basis of signals R and G, the reconstruction device 72, as described in further detail below, generates a reconstructed signal B', which is conducted to the output control 73. In addition, signal B, generated by the image sensor 53 and prepared by the signal preparation device 71, is conducted to the output control 73. Signal B in this example, however, contains no information on configuring the medical object 10 by means of white light, but instead image data for configuring the medical object 10 in fluorescent light.

Controlled by the mode control 75, the output control 73 can control the image output device 79 in such a way that either only a reconstructed white light image or only an image of the medical object 10 in fluorescent light, or simultaneously the reconstructed white light image and the image in fluorescent light, are depicted by the image output device 79. The reconstructed white light image is thus composed of the color values or image data acquired by the image sensor 53 for the color channels R and G, and the color values for the reconstructed color channel B'. The image in fluorescent light is formed only from the color values for the color channel B acquired by the image sensor 53.

Both a single depiction of an image in fluorescent light and a combined depiction of superimposed images in white light and in fluorescent light are possible with a false-color depiction of the fluorescent light image. For example, image points in which the intensity of the fluorescence exceeds a predetermined threshold are depicted in a highly or maximally saturated color that does not otherwise appear in the medical object 10.

Figure 3:
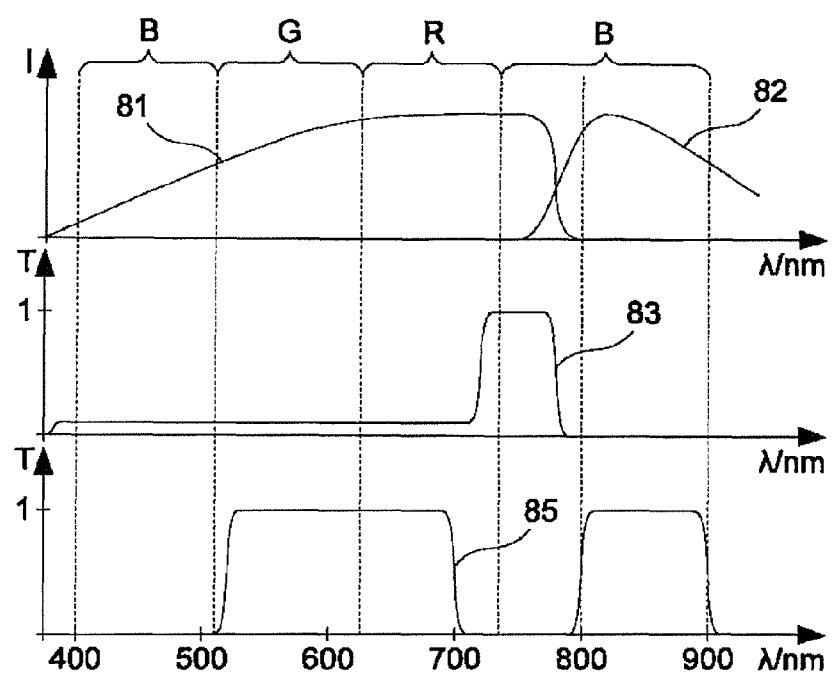
FIG. 3 is a schematic depiction of emission and transmission spectra.

FIG. 3 presents a schematic depiction of emission and transmission spectra of the light source 31, of a fluorescence of the medical object 10, of the illumination filter 32 and of the observation filter 52. The wavelength c in nm is shown on the abscissas, the intensity I or transmission degree T is shown as ordinates. Because of the relative alignment of the abscissas, only the lowest abscissa is labeled.

Above the topmost diagram in FIG. 3, figures within curly brackets indicate approximations to the wavelength ranges in which the sensors of the image sensor 53 associated with color channels B, G, R are sensitive. The example shown in FIG. 3 is based on an image sensor 53 whose sensors associated with color channel B are sensitive not just in the blue wavelength range in the area of 400 nm to 510 nm but also in a wavelength range of below 800 nm to about 900 nm.

The top diagram shows the intensities I in arbitrary units for the emission of the light source 31 and the fluorescence of the medical object 10 or of a fluorescent colorant contained in it. Because both intensities depend on geometric and other factors, both spectra are purely qualitative. Spectrum 81 of the light source 31 includes wavelengths of color channels B, G, and R between approximately 400 nm and 800 nm. Spectrum 82 of the fluorescence includes wavelengths of less than 800 nm to far over 900 nm with a maximum of about 820 nm. It corresponds approximately to the fluorescent spectrum of indocyanine green (ICG). The sensors associated with color channel B are thus suited for acquiring the fluorescence.

The center diagram in FIG. 3 shows the wavelength dependency of the transmission degree 83 of the illumination filter 32. The transmission degree 83 of the illumination filter 32 in large parts of the wavelength ranges associated with the color channels G and R comprises essentially no wavelength dependency or only a minor wavelength dependency. Light in this wavelength range is also designated here as illumination light. In the illustrated example the transmission degree 83 of the illumination filter 32 in the blue range of about 400 nm to about 500 nm comprises a similar size. Departing from this range, however, the transmission degree 83 of the excitation filter 32 in the blue range can be lower or zero or close to zero.

In a range of more than 700 nm to below 800 nm, the transmission degree 83 of the illumination filter 32 is essentially higher, in particular approximating a maximum (T≈1=100%). Light in this wavelength range is also designated here as excitation light. In the wavelengths relevant for excitation of the fluorescent colorant, an essentially higher illumination intensity is therefore produced in order to achieve a high intensity of fluorescence even at low concentration and/or low quantum efficiency of the fluorescent colorant, corresponding at least approximately to the intensity of the remission of green and red light.

The bottom diagram in FIG. 3 shows the transmission degree 85 of the observation filter 52 depending on the wavelength. The transmission degree 85 of the observation filter 52 is between about 500 nm and about 700 nm for most wavelengths and between about 800 nm and about 900 nm as a maximum (T≈1). In the ranges in which the transmission degree 83 of the illumination filter 32 is increased, the transmission degree 85 of the observation filter 52 is zero or close to zero, in order to block the portions of the light foreseen for exciting the fluorescent colorant that are remitted by the medical object 10. In addition, the transmission degree 85 of the observation filter 52 in the blue range from about 400 nm to about 500 nm is zero or essentially zero, to prevent the sensors of the image sensor 53 that are associated with the color channel B from receiving remitted blue light.

With the selected characteristics of the illumination filter 32 and of the observation filter 52, the sensors of the image sensor 53 that are associated with color channels G and R essentially acquire the green or red portion of the illumination light (also designated as white light, which here only covers wavelengths of about 700 nm, however) remitted from the medical object 10, but neither remitted excitation light nor fluorescent light. The sensors of the image sensor 53 that are associated with color channel B essentially acquire exclusively fluorescence that is emanating from the medical object 10 or from fluorescent colorant in the medical object 10.

Thus, light remitted from the medical object 10 is not acquired with the wavelengths of the color channel B. In other words, color channel B is not available for acquiring image data that produce a balanced or natural color impression. To achieve a balanced or natural color impression, image information or color values are reconstructed for color channel B, as described more fully below with reference to FIG. 5. This is also referred to as reconstruction of a white light image.

Figure 4:
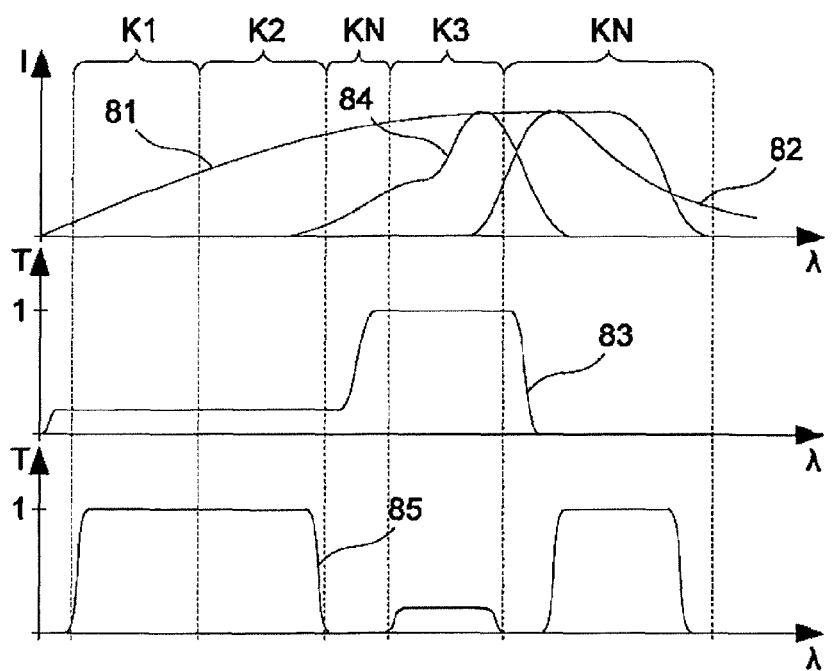
FIG. 4 is a schematic depiction of emission, absorption, and transmission spectra.

FIG. 4 shows a schematic depiction of intensities I and transmission degrees T for an additional embodiment. Again the wavelength c in nm are associated with the abscissas and the intensity I or the transmission degree T is associated with the ordinates. The abscissas are relatively aligned with one another, but are not absolutely labeled, because the example depicted in FIG. 4 is independent of concrete wavelengths.

Above the topmost diagram of FIG. 4 the wavelength ranges are indicated with curly brackets, inside which the sensors of the image sensor 53 associated with color channels K1, K2, K3, and KN are sensitive. The filter characteristics described below can be extended correspondingly to situations with additional color channels K4, K5, and so on.

In the top diagram are shown the wavelength dependencies of intensities I, of the emission from the light source 31, of the absorption of fluorescent colorant in the medical object 10, and of the fluorescence of the fluorescent colorant. Spectrum 81 of the light source 31 essentially includes all wavelengths associated with color channels K1, K2, K3, KN. Absorption spectrum 84 includes wavelengths that are associated with color channels K3, KN, but lies primarily in color channel K3. Spectrum 82 of fluorescence essentially includes wavelengths that are associated with color channel KN.

The wavelength dependency of the transmission degree 83 of the illumination filter 32 is illustrated in the center diagram. The transmission degree 83 of the excitation filter 32 comprises a first, low value within the wavelengths associated with color channels K1, K2. At wavelengths associated with color channel K3, the transmission degree 83 comprises a second, high value. At higher wavelengths that are associated with color channel KN and lie in the range of spectrum 82 of the fluorescence of the fluorescent colorant, the transmission degree 83 of the illumination filter 32 is zero or essentially zero.

Light in the wavelength ranges of color channels K1 and K2 is also designated here as illumination light. Light in the wavelength ranges of color channel K3 serves to excite fluorescent colorant and therefore is also designated here as excitation light. However, remission of the excitation light from the medical object can also be observed in this example.

The bottom diagram shows the transmission degree 85 of the observation filter 52. Its transmission degree 85 comprises a high value T≈1 at wavelengths associated with color channels K1, K2, and KN. At wavelengths associated with color channel K3 their transmission degree 85 has a low value. The transmission degrees 83, 85 of illumination filter 32 and of observation filter 52 are selected, for example, in such a way that, at wavelengths associated with color channels K1, K2, K3, the product of the transmission degrees 83, 85 is essentially independent of wavelength. At all wavelengths that are associated with color channel KN and in which the transmission degree 83 of the illumination filter 32 is not essentially zero, the transmission degree 85 of observation filter 52 is zero or essentially zero in order to block light remitted from the medical object 10.

With the filter characteristics illustrated in FIG. 4, the sensors of image sensor 53 that are associated with color channels K1, K2, K3 receive, exclusively or essentially exclusively, light remitted from the medical object 10. The sensors of image sensor 53 that are associated with color channel KN receive, exclusively or almost exclusively, fluorescent light emanating from the medical object 10 or from the fluorescent colorant in the medical object 10.

Thus, light remitted from the medical object 10 is not acquired with the wavelengths of color channel KN. In other words, color channel KN is not available for acquiring image data that produce a balanced or natural color impression. To achieve a balanced or natural color impression, image information or color values for color channel KN are reconstructed, as explained in greater detail hereafter with reference to FIG. 5. This can also be designated as reconstruction of a white light image.

Figure 5:
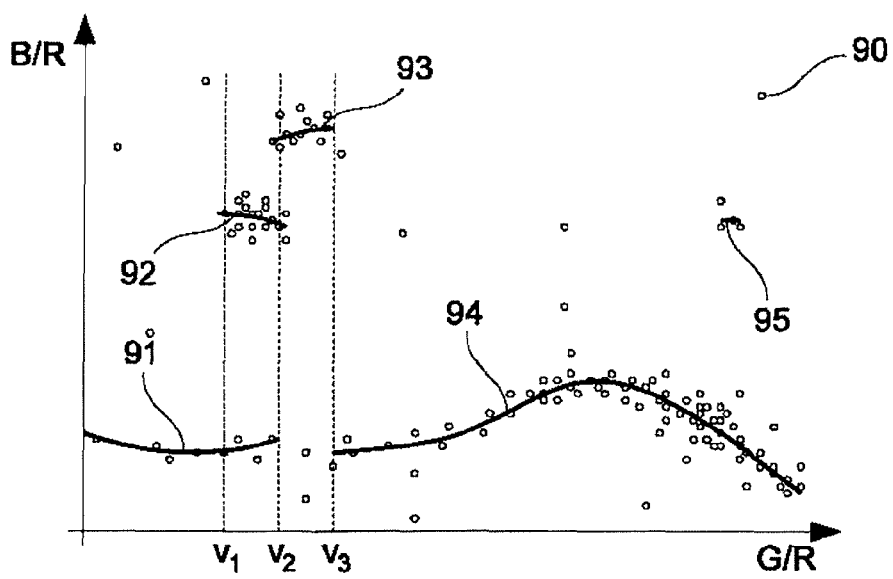
FIG. 5 is a schematic depiction of reference image data.

FIG. 5 shows a schematic depiction of reference image data. Here the image data for one image point of a reference image are represented in each case by a small circle 90. Shown in the abscissa is the ratio G/R between the color value for color channel G and the color value for color channel R. The ordinates show the ratio B/R between the color value for color channel B and the color value for color channel R. The number of image data 90 is strongly understated with respect to a real image sensor at $10^5$ to $10^7$ image points or pixels. Because of the quantification of color values—usually full-row values between zero and 255 are used—several image data can lie at one and the same point in the diagram.

To obtain the diagram shown in FIG. 5, a reference image of a reference object is first acquired with the image sensor 53. Here the reference object is illuminated with white light or light with another predetermined illumination spectrum, at which a color impression emerges that is experienced by the observer as natural or balanced. In the reference image, relevant image areas can be selected, irrelevant image areas excluded or various image areas can be evaluated differently depending on relevance. Image areas are relevant, for example, in cases where they depict tissue or have medical relevance in other ways. Irrelevant image areas are those that show instruments, teeth, or other objects that are medically irrelevant for the foreseen application. High relevance is accorded to objects whose reproduced color fidelity is important, whereas objects whose reproduced color fidelity is less important or unimportant are assigned a lower relevance.

All image data for image points from non-rejected image areas are depicted in the diagram shown in FIG. 5. Accumulations of image data are identified, whereas image data in areas of the diagram with a low density of image data are ignored. A relation is adjusted or a function is fitted for the accumulations; for instance, a cubic spline is calculated. In some cases the originally determined relevance for each image point is taken into account. Adjustments can be made to the relation in certain segments or globally. Image data lying far removed from an accumulation can be disregarded.

The adjusted relation can be selected in such a way that it is unequivocal for each G/R value. In the example shown in FIG. 5 this is the case, among others, for a first segment 91 for G/R<v1. However, several accumulations of image data can also be evaluated in such a way that several adjusted relations exist for one value of G/R. This is the case, for instance, for a first segment 91 and a second segment 92 for v1<G/R<v2, for the second segment 92 and a third segment 93 in a small area around G/R=v2, and for a fourth segment 94 and a fifth segment 95 in a small interval of G/R.

Segments 91, 92, 93, 94, 95 of the adjusted relation are transmitted into an unequivocal or equivocal lookup table. In the present example, the lookup table must include several entries, or be equivocal, in the area of the second segment 92 and in the area of the fifth segment 95. Instead of a lookup table, for instance, the parameters of the adjusted relation can be entered.

A corresponding evaluation of image data is also possible in other color spaces, for instance in the HSV or CMYK color space. The normalization of the color values to color channels G and B with the color value for color channel R, seen in FIG. 5, is advantageous in medical applications, because red tones dominate and therefore the values of G/R and B/R are predominantly less than 1. Thus the normalization with the color value to color channel R approximately constitutes a normalization to brightness, which in endoscopic applications for instance depends on the distance of the object from the distal end of the endoscope. In using the HSV model, for instance, H and S would have been entered in relation to one another. With a total of only two color channels, for instance, a normalization is possible with the sum of both color values or with a sum of both color values averaged in a predetermined area around the chosen image point.

The evaluation as depicted in FIG. 5 occurs for instance with reference to one or more reference images, which are representative for images acquired for a predetermined application, or else with reference to one or more reference images acquired at times when no fluorescence was excited, no fluorescent light was emitted, but rather the object was illuminated with white light and observed without a filter that modifies a white light spectrum. The last-mentioned conditions are also designated as white light mode. This mode can for instance be controlled or used in alternation with a fluorescent mode. In fluorescent mode, then, the lookup table produced in the last preceding white light mode can be used in each case.

Figure 6:
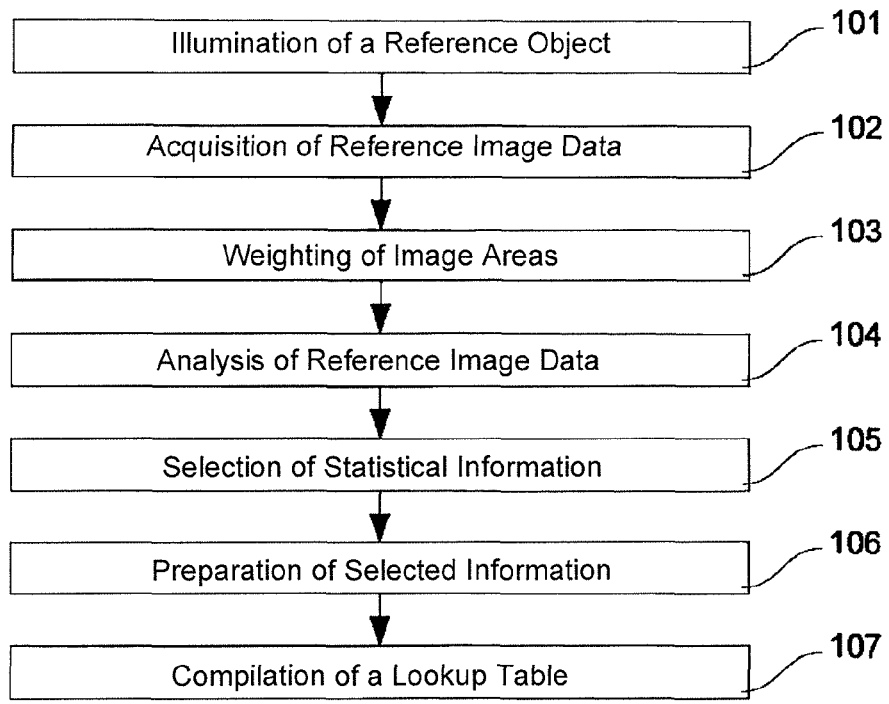
FIG. 6 is a schematic flow diagram of a method for generating a lookup table.
Figure 7:
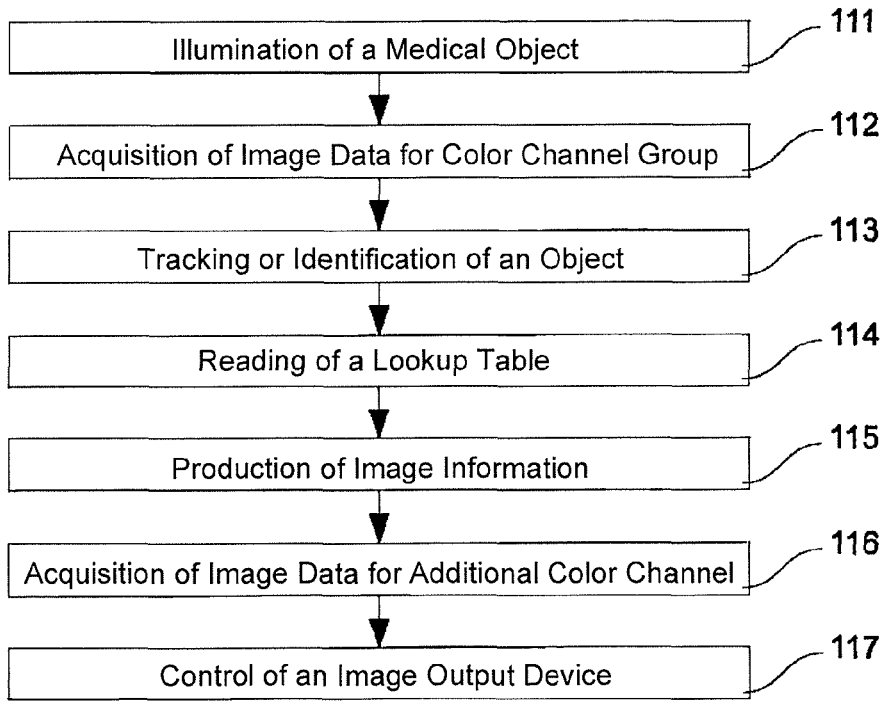
FIG. 7 is a schematic flow diagram of a method for controlling a multi-color output of an image of a medical object.

FIGS. 6 and 7 show schematic flow diagram of a method for forming a lookup table or a method for controlling a multi-color output of an image. Both methods can be combined in operating an apparatus for controlling a multi-color output, and in particular can be executed in immediate succession to one another or in alternation. Although both methods can be executed also with apparatuses, filter characteristics, and color spaces that differ from the ones shown above in FIGS. 1 to 5, reference numerals from FIGS. 1 to 5 are used below to facilitate clarity.

For a method for creating a lookup table, in a first step 101a reference object is illuminated with white light or light with another predetermined spectrum. In a second step 102, reference image data are acquired. In a third step 103, image areas in the reference image are weighted and/or selected and/or rejected according to their medical relevance or according to the importance of their color-faithful or natural depiction.

In a fourth step 104, the reference image data that have not been rejected are analyzed. For example, accumulations are identified, the color space is exchanged or mathematical transformations are undertaken. In a fifth step 105, statistical information is selected from the analyzed reference image data. Here, in particular, those reference image data are taken into account that are similar to many other reference image data. This is indicated in the accumulations described in the depiction of FIG. 5. Here the relevance for each individual image point can be taken into account.

The first step 101, the second step 102, the third step 103, the fourth step 104, and the fifth step 105 can be repeated for several reference objects and several images of one or more reference objects.

In a sixth step 106, the selected statistical information is prepared, for instance by a cubic spline or adaptation to another relation. Here, again, for each image point its relevance can be considered. In a seventh step 107, a lookup table is produced from the prepared selected information. This lookup table contains, for instance, one or more values of B/R for every value of G/R, or one value of B for every value pair of R and G. Instead of a lookup table, a mathematical function or relation can be entered. The lookup table or mathematical function or relation can be used in the following method explained with reference to FIG. 7.

In many applications, a method can be repeated wholly or partly, periodically or aperiodically, as explained above in relation to FIG. 6. For instance, the method can always be repeated if the medical object is illuminated with white light or light with another predetermined spectrum that produces a natural or balanced color impression without reconstruction of a color channel (hereafter also referred to as white light mode). Another condition is that no observation filter is used, or else an observation filter 52 that does not distort the color impression, in particular one that comprises a transparency that is nearly uniform in all color channels.

FIG. 7 shows a schematic flow diagram of a method for controlling a multi-color output of an image of a medical object. In a first step 111, the medical object is illuminated with an illumination spectrum. In a second step 112, image data, in particular color values, are acquired for a group of one or more color channels by means of an image sensor 53.

In an optional third step 113, the medical object or a part of the medical object within the image is identified, for instance by using algorithms that are known as object recognition. Alternatively or in addition, one object can be pursued through several successively acquired images. Then a lookup table of its own or its own part of a lookup table, which for instance was drawn up with a residual white light mode as described above with reference to FIG. 6, can be associated with the object.

In a fourth step 114, on the basis of the color values acquired in the second step 112 for the group of one or more color channels, a color value is read for an additional color channel, for which no color value was acquired in the second step 112. Here a lookup table can be selected from several lookup tables or one of several entries in a lookup table on the basis of the identity of an object with which the particular image point is associated, as determined in the third step 113. For equivocal data, such as occur as described above in connection with FIG. 5 for G/R=v2, image data or color values for surrounding image data can be taken into account. If G/R>v2 is valid in most cases for surrounding image points, the entry in the lookup table corresponding to segment 93 is read for B/R; if G/R<v2 is predominantly valid for surrounding image points, the entry corresponding to the second segment 92 is read. For v1<G/R<v2, for instance on the basis of the identity of the object with which the image point is associated, a decision is made as to whether the entry associated with the first segment 91 or the entry corresponding to the second segment 92 should be read.

In a fifth step 115, on the basis of the value read from the lookup table in the fourth step 114, image information is produced, for instance by calculating a color value for the color channel B from the read value of B/R and the color value for color channel R. In a sixth step 116, image data, in particular color values, are acquired for an additional color channel. In the example depicted on the basis of FIGS. 2 and 3, the color value would be acquired for the color channel B with which fluorescent light is associated. In a seventh step 117, an image output device 79 is controlled in order either to depict only one reconstructed white light image from the color values acquired in the second step 112 and the color value reconstructed in the fifth step 115, or only one image from the color value for fluorescence acquired in the sixth step 116, or both in succession or superimposed.

The illustrated methods and apparatuses can also be used for medical applications in which no fluorescence is acquired, and for non-medical applications, in order to reconstruct the most color-faithful reproduction possible in the absence of one color channel.

What is claimed is:

1. A method for controlling a multi-color output of an image of a medical object for assisting medical personnel, comprising the following steps:
    illuminating the medical object with light with an illumination spectrum;
    acquiring actual image data for a group of one or more color channels by means of an image sensor;
    acquiring at least one reference image data for an additional color channel by illuminating one or more reference objects with white light or light with another predetermined spectrum;
    correlating, using a processor, the one or more reference images and the actual image data;
    generating, using the processor, image information concerning the additional color channel based upon the ascertained correlation; and
    controlling an image output apparatus for multi-color output of the image, depending on the actual acquired image data and the generated image information for the additional color channel.

2. The method of claim 1, wherein the steps of illuminating and acquiring are performed by an endoscope probe.

3. The method of claim 1, wherein the image information for one image point at least is produced, either depending on the acquired actual image data for an image point or depending on acquired image data for surrounding image points.

4. The method of claim 1, wherein the image information is generated for one image point depending on the actual image data acquired at various points in time.

5. The method claim 1, wherein successive actual image data are acquired on several images of the medical object, and wherein the medical object or a part of the medical object is either identified or tracked in the several images at least, in order to associate image points with the medical object or part of the medical object, and wherein the image information is generated for one image point depending on the association of the image point with the medical object or with the part of the medical object.

6. The method of claim 1, wherein a lookup table is used to generate the image information.

7. The method of claim 1, wherein the medical object is the reference object, or wherein the reference object is typical with respect to its reciprocal effect with light for medical objects that are to be configured.

8. The method of claim 1, further comprising the steps of:
illuminating the medical object with an excitation spectrum that is different from the illumination spectrum;
acquiring additional image data for the additional color channel by means of the image sensor or another image sensor; and
controlling an image output device depending on the acquired additional image data or depending on the acquired actual image data, the generated image information, and the acquired additional image data.

9. The method of claim 8, wherein
the medical object emits fluorescent light on the basis of illumination with the excitation spectrum as the fluorescent light is acquired by the additional color channel.

10. The method of claim 9, wherein the fluorescence is excited with indo-cyanine green.

11. The method of claim 8, wherein only one video camera is used for acquiring image data, wherein the video camera comprises an image sensor for several color channels or several image sensors for one color channel each.

12. A non-transitory computer readable medium storing a computer program with program code for executing or controlling a method comprising the steps of:
illuminating the medical object with light with an illumination spectrum;
acquiring actual image data for a group of one or more color channels by means of an image sensor;
acquiring at least one reference image data for an additional color channel by illuminating one or more reference objects with white light or light with another predetermined spectrum;
correlating, using a processor, the one or more reference images and the actual image data;
generating, using the processor, image information concerning the additional color channel based upon the ascertained correlation; and
controlling an image output apparatus for multi-color output of the image, depending on the actual acquired image data and the generated image information for the additional color channel.

13. An apparatus for controlling a multi-color output of an image of a medical object, the apparatus comprising:
an illumination device for illuminating the medical object with light with an illumination spectrum and for illuminating one or more reference objects with white light or light with another predetermined spectrum;
one or more image sensors for acquiring actual image data for a group of one or more color channels and for acquiring at least one reference image data for an additional color channel;
a processor for correlating the one or more reference images and the actual image data and to generate the image information concerning the additional color channel based upon the ascertained correlation; and
a control for controlling an image output device for multi-color output of the image depending on the actual acquired image data and the generated image information for the additional color channel.

14. The apparatus of claim 13, wherein the one or more image sensors are endoscopic probes.

\* \* \* \* \*